United States Patent [19]
Streeter et al.

[11] Patent Number: 5,879,453
[45] Date of Patent: Mar. 9, 1999

[54] SYSTEM FOR VERIFYING THE IDENTITY OF AN APPLICANT THROUGH THE USE OF FINGERPRINTS

[75] Inventors: Anthony P. Streeter, Carol Stream; Thomas D. Gordon, DeKalb, both of Ill.

[73] Assignee: Wallace Computer Services, Inc., Hillside, Ill.

[21] Appl. No.: 908,968

[22] Filed: Aug. 8, 1997

[51] Int. Cl.[6] ................................................ B41K 1/00
[52] U.S. Cl. ........................ 118/31.5; 283/68; 283/69; 283/70; 283/78
[58] Field of Search .................. 118/31.5, 264; 427/1; 283/68–70, 78

[56] References Cited

U.S. PATENT DOCUMENTS

| | | |
|---|---|---|
| 1,459,634 | 6/1923 | Miller . |
| 1,499,995 | 7/1924 | Merritt . |
| 1,746,955 | 2/1930 | Messer . |
| 1,810,493 | 6/1931 | Messer . |
| 2,153,684 | 4/1939 | Ballard ................................. 118/31.5 |
| 2,500,612 | 3/1950 | Krogh ................................... 118/31.5 |
| 3,318,282 | 5/1967 | Bean ........................................ 118/9 |
| 3,318,428 | 5/1967 | Klein ....................................... 194/2 |
| 3,419,287 | 12/1968 | Rudie ...................................... 283/7 |
| 3,709,524 | 1/1973 | McKee et al. ...................... 118/31.5 |
| 3,831,552 | 8/1974 | Schmidt et al. .................... 118/31.5 |
| 3,897,749 | 8/1975 | May et al. ........................... 118/31.5 |
| 4,029,012 | 6/1977 | Smith, III et al. ................... 101/368 |
| 4,182,261 | 1/1980 | Smith, III et al. ................. 118/31.5 |
| 4,379,178 | 4/1983 | Meadows et al. ..................... 427/1 |
| 4,650,219 | 3/1987 | Sigman ................................ 283/70 |
| 4,669,753 | 6/1987 | Land et al. ........................... 283/68 |
| 4,699,077 | 10/1987 | Meadows et al. ................. 118/31.5 |
| 4,702,194 | 10/1987 | Martin et al. ..................... 118/31.5 |
| 4,705,299 | 11/1987 | Hedgcoth et al. .................... 283/68 |
| 4,721,628 | 1/1988 | Pieper ..................................... 427/1 |
| 4,917,987 | 4/1990 | Arndt et al. ......................... 430/139 |
| 4,983,415 | 1/1991 | Arndt et al. ........................... 427/1 |
| 5,067,749 | 11/1991 | Land ..................................... 283/68 |
| 5,071,168 | 12/1991 | Shamos ............................... 283/117 |
| 5,160,171 | 11/1992 | Gregory et al. ..................... 283/91 |
| 5,193,855 | 3/1993 | Shamos ............................... 283/117 |
| 5,194,289 | 3/1993 | Butland .................................. 427/1 |
| 5,330,231 | 7/1994 | Godfrey ............................... 283/78 |
| 5,395,444 | 3/1995 | Arndt et al. ........................ 118/31.5 |
| 5,454,600 | 10/1995 | Floyd .................................... 283/78 |
| 5,462,597 | 10/1995 | Jubran ................................ 118/31.5 |
| 5,709,746 | 1/1998 | Ballard ............................... 118/31.5 |

OTHER PUBLICATIONS

Brochure entitled "IdentaPrint –Security Identification System", IdentaPrint, Garland, Texas, Published prior to Aug. 8, 1997.

*Primary Examiner*—Laura Edwards
*Attorney, Agent, or Firm*—Roylance, Abrams, Berdo & Goodman, L.L.P.

[57] ABSTRACT

A system and corresponding method for obtaining fingerprint samples of a person completing an application form and using those samples to verify that person's identity. The system employs an application form, such as a life insurance application, job application, banking or checking account application, and so on, comprising a first substrate having a fingerprint information receiving area adaptable to receive a fingerprint image of a finger of the person completing the application. The system further employs a second form, such as a chain of custody form, comprising a second substrate having an area adaptable to receive thereon a fingerprint image of the finger of the person. Preferably, an inkless fingerprint kit is used to provide the fingerprint samples on both forms. The fingerprint samples can be compared either manually or through the use of a computer to verify whether the same person provided the samples on both forms.

21 Claims, 9 Drawing Sheets

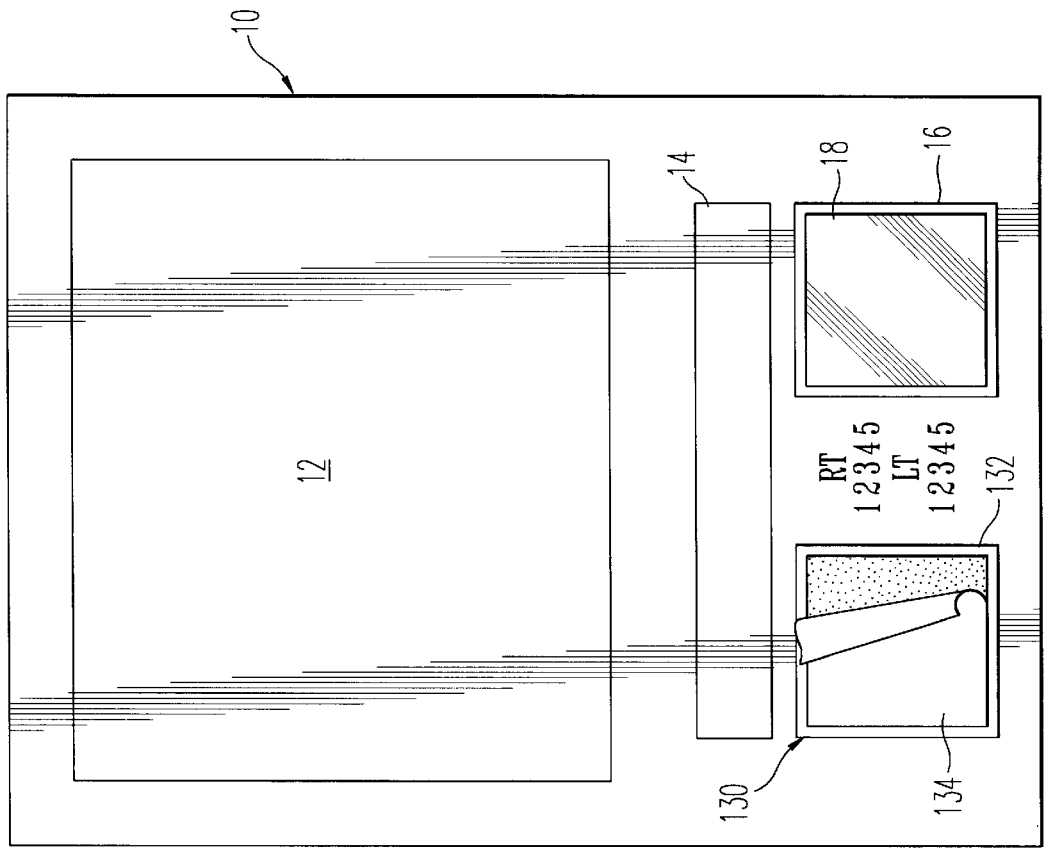
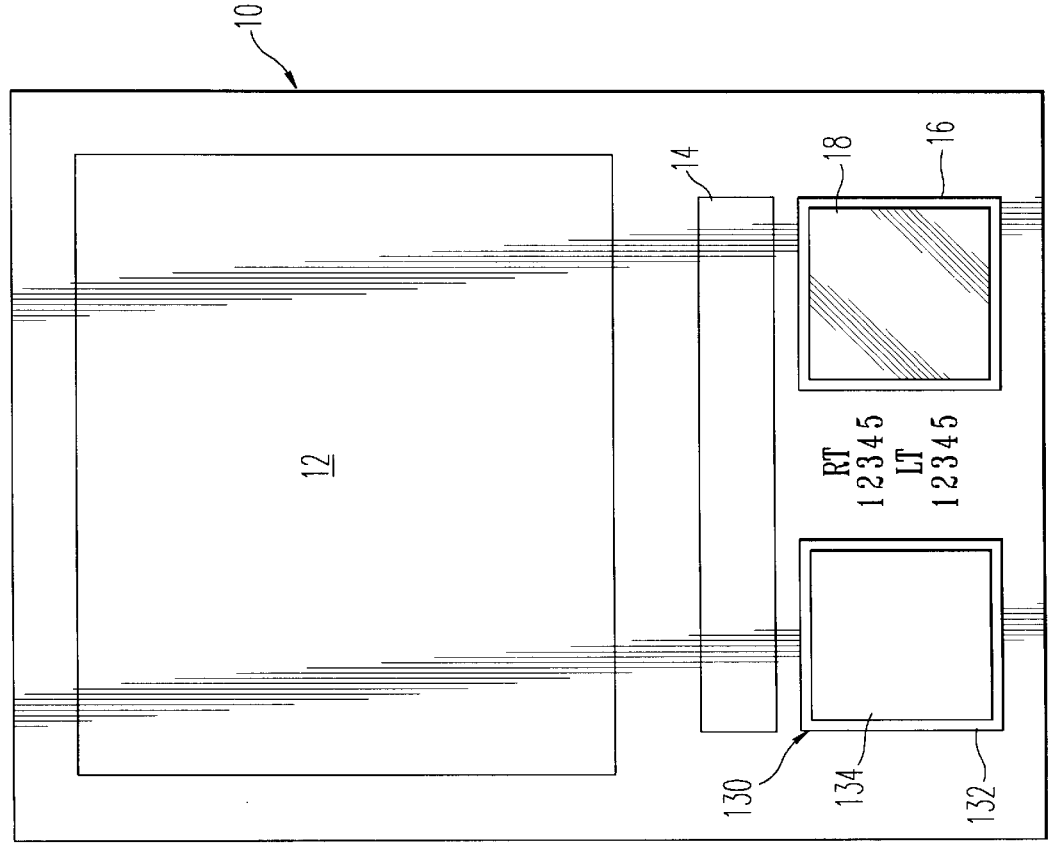

SYSTEM FOR VERIFYING THE IDENTITY OF AN APPLICANT THROUGH THE USE OF FINGERPRINTS

BACKGROUND OF THE INVENTION

1. Field of the Invention

The present invention relates to a system and method for obtaining fingerprint samples of a person completing an application form, and using those samples to verify that person's identity. More particularly, the present invention relates to a system and corresponding method in which a fingerprint sample of a person completing an application form is taken and stored for comparison with another fingerprint sample provided by that person on a different document to verify that the same person provided both samples.

2. Description of the Related Art

Various institutions such as insurance companies, banks, and credit companies are victimized by fraudulent schemes every year, and as a result, suffer millions of dollars of losses annually. Perhaps one of the most common schemes that occurs, especially in the insurance and banking arena, involves the use of an impostor or "stand-in" who misrepresents his or her identity in order to cash another person's check, use another person's credit card, or assist an ailing person in obtaining life insurance.

For example, most insurance companies require that an applicant wishing to obtain a life insurance policy undergo a physical examination prior to issuance of the policy. If the individual applying for insurance policy has an ailment which would ordinarily preclude that person from being eligible for life insurance, that person can use a "stand-in" to undergo the physical examination in that person's place. That is, although the actual insurance applicant will fill out the insurance form, a "stand-in" having no major ailment will undergo the physical examination and provide the necessary samples of urine, blood, and the like. Since the tests performed on those samples will reveal no ailments, the insurance applicant will be issued the insurance policy. If the applicant then dies due to his or her ailment, the insurance company will find it difficult to prove that the insured person was suffering from that ailment prior to obtaining the insurance policy, and thus will be forced to pay the insurance claim.

Although insurance companies currently use precautionary measures such as checking an individual's picture identification when the application for the insurance policy is being completed and when the individual is undergoing a physical examination, it is not uncommon for a stand-in to use false identification to misrepresent himself or herself as the applicant. Also, even though insurance companies require the applicant's signature on the insurance policy, it is often not difficult for a stand-in to forge the applicant's signature when signing the physical examination form. Furthermore, even though some insurance companies may include a copy of the applicant's photo identification with the application which the person performing the physical examination can use to verify whether the person being examined is indeed the applicant, a stand-in who's appearance closely resembles the applicant can be used to avert these precautionary measures.

A job applicant also may find it desirable to use a stand-in. For example, many private companies now require potential employees to undergo a physical examination and drug screening prior to being hired. Often the examination is conducted at a clinical laboratory not associated with the company. Hence, the person at the laboratory performing the examination and obtaining urine and blood samples has no way of positively identifying whether the individual providing the samples is the actual job applicant. Although most laboratories will require that the individual providing the sample present picture identification, as discussed above, it is often easy to obtain false identification.

In the banking and credit arena, it is not uncommon for a person with criminal intent to successfully cash a check or use a credit card of another illegally. Even though many banks and financial institutions require that an individual cashing a check or using a credit card present identification, false identification is often easy to obtain. Hence, previous efforts to prevent bank and credit card fraud have proven unsuccessful, because many financial institutions still suffer millions of dollars of losses each year due to illegal check cashing and credit card use.

In addition to a person's signature, photo identification and the like, it is known that a person's fingerprint can be used to verify that person's identity. For instance, as discussed in U.S. Pat. Nos. 5,071,168 and 5,193,855 to Shamos, it is known for a hospital to take a fingerprint image of a patient so that that patient's identity can be verified when, for example, the patient is providing a specimen or undergoing a procedure at the hospital. Also, U.S. Pat. No. 3,318,428 to Klein discloses that it is known to capture a fingerprint image of a person purchasing a ticket on both the ticket and on a permanent record, so that the ticket purchaser's identity can be verified at a later date.

It is also known to request a fingerprint sample from a person in addition to that person's signature when the person is completing, for example, a document used in business. For instance, an insurance company may ask a person to provide a fingerprint sample on the application form in addition to that person's signature, while a bank may request that a person attempting to cash a check provide a fingerprint sample on the check. Also, as described in the Shamos patents discussed above, a person may be asked to provide a fingerprint sample when giving a specimen at a hospital or other medical facility.

Although these practices may be helpful in positively linking a single individual to a single document (e.g., an insurance applicant to an insurance form, a ticket purchaser to a ticket, and so on), a continuing need exists for an efficient system or process for positively verifying the identity of a person who is intended to handle several documents relating to a common transaction at different times and at different locations. For example, a continuing need exists for an efficient system and process for positively identifying an applicant, such as an insurance policy applicant, throughout various stages of the application process.

Additionally, it is often desirable to be capable of positively linking a donor, such as a blood donor, to the donated sample or specimen to be able to positively identify that the sample or specimen came from the donor. This is particularly crucial when a person about to undergo an operation donates blood that he or she intends to be used during that operation.

Typically, the bag or bags of donated blood will be stored at the hospital in which the operation is to be performed. The bags will generally include a label or sticker including the name, birthdate, social security number, and so on, of the person who donated the blood. However, if the labels are mismarked or misread, the person can inadvertently receive the wrong blood.

Accordingly, a continuing need exists for an effective system which will positively link a blood donor to the donated blood.

SUMMARY OF THE INVENTION

The present invention provides a system and method for obtaining samples of a person's fingerprint on different documents at different times, and using those samples to verify that the multiple samples were provided by the same person. In particular, the system of the present invention preferably employs an inkless fingerprinting system that is capable of obtaining a fingerprint image on a substrate. The substrate can be removably attached to another medium so that the substrate can be moved from the medium to which it is originally attached to a second medium such as a business form.

According to one embodiment of the invention that relates to the insurance industry, the system includes an insurance form comprising a substrate having a personal information area in which information pertaining to the insurance application is entered, and a fingerprint receiving area onto which a fingerprint image can be applied. Specifically, the fingerprint receiving area of the substrate can be coated directly with an inkless fingerprint developing coating, or alternatively, the inkless fingerprint developing coating can be present on another substrate that can be attached to the fingerprint receiving area.

The individual applying for the insurance policy will be requested to provide a fingerprint at the fingerprint receiving area Preferably, the individual will place a finger on an applicator pad including an inkless fingerprint material which will coat the surface of the person's finger upon contact. The person will then place the coated finger onto the inkless fingerprint developing coating, which will react with the coating on the person's finger to create a fingerprint image. If the inkless fingerprint developing coating is present on the insurance form, the fingerprint image will thus appear directly on the insurance form. Alternatively, if the inkless fingerprint developing coating is present on a substrate of another medium, that substrate on which the fingerprint image is formed will be attached to the fingerprint receiving area of the insurance form.

The system further includes a second form that is used when the insurance applicant provides samples such as urine, blood and the like during the physical examination that the insurance company will require prior to issuing the policy. The second form comprises a second substrate having a personal information area on the surface thereof in which information pertaining to the individual providing the specimen can be entered. The second substrate further includes a fingerprint receiving area on the surface thereof for receiving a fingerprint of the person giving the specimen. An inkless fingerprint developing coating can be present directly on the fingerprint receiving area or on a substrate of another medium. The person providing the samples will be asked to place a finger on an applicator pad as described above so that the finger will become coated with an inkless fingerprint coating. Of course, the finger being used to provide this fingerprint image on the second substrate preferably will be the same finger that was used to provide the fingerprint image on the insurance form in the manner described above.

The person will then place that finger onto the fingerprint developing coating so that the fingerprint image will be formed by the reaction between the coating on the finger and the developing coating. If the fingerprint developing coating is directly on the fingerprint receiving area, the fingerprint image will appear in that area. However, if the developing coating is on another substrate, that substrate can be attached to the fingerprint receiving area of the second substrate.

It is noted that in both instances, a coloring agent or material can be added to the developing coating, inkless fingerprint coating, or both, so that the fingerprint image will appear in a desired color. For example, the material can be such that the fingerprint image is either visible or substantially invisible to the human eye under normal lighting conditions, and fluoresces when irradiated with ultraviolet light.

The two fingerprint images can then be compared to each other at a desired time (e.g., in the event that suspicion arises as to the insurance applicant's identity) to determine whether the fingerprints match. A fingerprint identification form can be used as an initial tool in assisting in the comparison of the fingerprints. Alternatively, the fingerprints can be scanned by a scanning device so that data representing the fingerprints can be entered into a computer running fingerprint identification software which will enable the computer to compare the fingerprint images to determine whether they match. If the fingerprints do not match, it can be ascertained that the fingerprint image in the fingerprint receiving area of the first substrate and the fingerprint image in the fingerprint receiving area of the second substrate came from different people, and the appropriate action can be taken.

A system and process similar to that described above can be used in other areas, such as in employment, banking, and so on. For example, a job applicant can complete an employment application and be requested to provide a fingerprint sample in the manner described above with regard to an insurance application. If the company requires that potential employees undergo a physical examination and, in particular, a drug screening, the job applicant will be requested to provide a fingerprint sample in the manner described above when undergoing the physical examination and providing urine and blood samples. Hence, the fingerprint samples can be compared with each other to verify that the job applicant indeed underwent the physical exam and provided the urine and blood samples. Alternatively, instead of providing the fingerprint sample on the employment application, the job applicant can be asked to provide another fingerprint sample if suspicion arises after the test results have been completed. In this event, the fingerprint sample or the form used during the examination will be compared with this new fingerprint sample.

In the banking arena, a person opening a checking account at a financial institution, for example, can be requested to provide a fingerprint sample on the checking account application in the manner described above with regard to an insurance application, and the application can be filed in accordance with the institution's normal procedures. A person cashing a check at that institution that has been issued in the name of the applicant will be required to provide a fingerprint on the check by using, for example, and inkless fingerprint system such as that described above. The fingerprint on the check can be compared with the fingerprint on the account application to verify whether the person cashing the check is indeed the person to whom the account belongs.

The fingerprint identification kit according to the present invention can also be used to positively link a person donating blood to the donated blood, in particular, when that person wants his or her own blood to be given to him or her during an operation. The person donating the blood will place a fingerprint image on a portion of a donation form, such as a removable card, when the blood is donated. The person will also place a fingerprint image on a label which will be attached to the bag in which the donated blood is stored. The portion of the form (e.g., the removable card) on which the fingerprint has been placed is given to the person. When the person is admitted to the hospital for the operation, the person will present the card having the fingerprint image to the person processing the admission. The fingerprint image on the card will be compared with the image on the blood bags to assure that the fingerprints match and thus confirm that the person is being given his or her own donated blood.

BRIEF DESCRIPTION OF THE DRAWINGS

These and other objects and advantages of the invention will become more apparent and more readily appreciated from the following detailed description of the presently preferred exemplary embodiments of the invention taken in conjunction with the accompanying drawings, of which:

FIG. 14 is a top plan view of a form on which a fingerprint image is received, having an applicator attached thereto, according to an embodiment of the present invention;

FIG. 15 is a top plan view of the form shown in FIG. 14 with the cover of the applicator being removed to expose the developing coating.

DETAILED DESCRIPTION OF THE PREFERRED EMBODIMENTS

Figure 1:
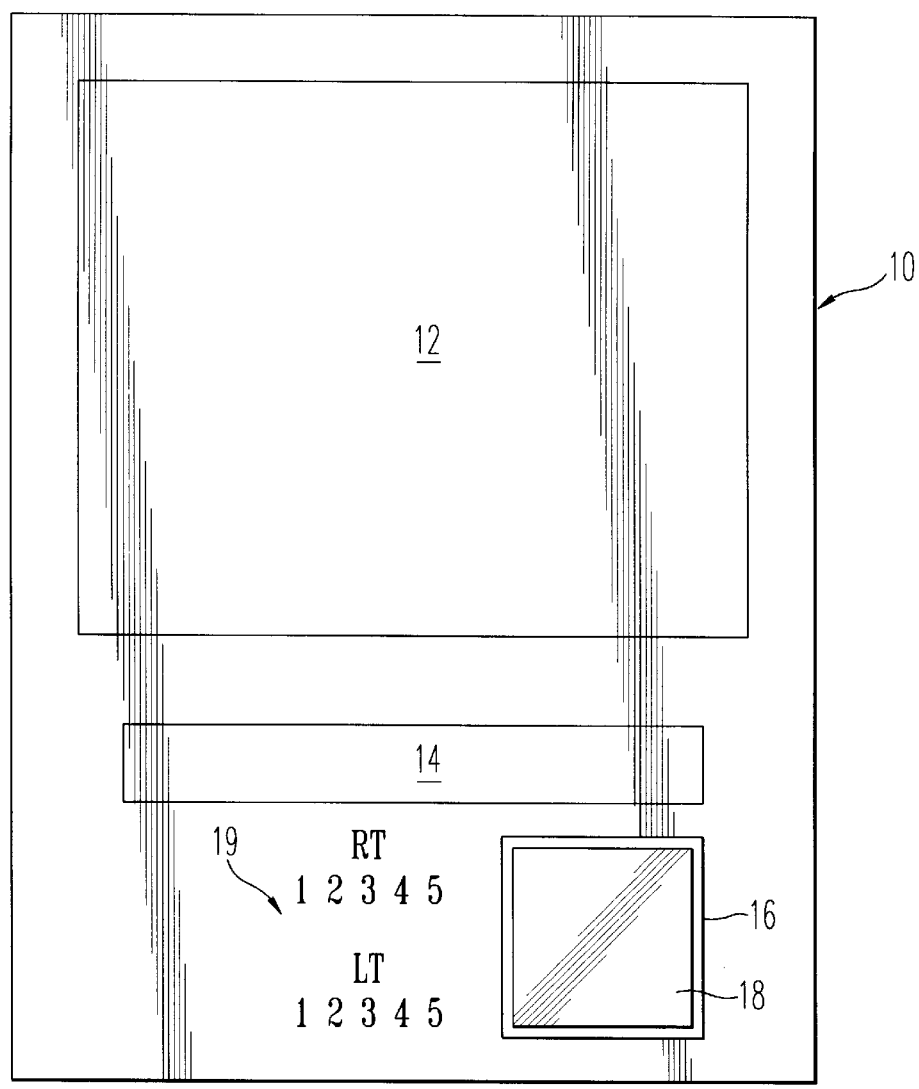
FIG. 1 is a top plan view of a form having at least one fingerprint receiving area which is used in a system according to an embodiment of the present invention.

FIGS. 1–10 illustrate examples of the forms and equipment that are employed in the system according to an embodiment of the present invention. Specifically, FIG. 1 illustrates an example of a signature page of an application form 10, such as a life insurance application form, employment application form, and so on. The application form 10 includes a section 12 in which personal information about the applicant can be entered, such as the applicant's name, address, date of birth and answers to specific health questions, and a signature section 14 which receives the applicant's signature. Although for exemplary purposes, the form 10 is described below as a life insurance application form, the form 10 can be any type of application form, such as an employment application, checking or banking account application, vehicle rental application, welfare application, and so on. The term "application" in this specification can be construed as referring to any of these types of applications.

According to this embodiment of the present invention, the application form 10 further includes a fingerprint image receiving area 16 at which the applicant will be required to provide a fingerprint image for identification purposes. Specifically, fingerprint image receiving area 16 can include an inkless fingerprint development coating 18 for developing an image of a fingerprint of a finger of the insurance applicant whose signature is entered in signature section 14. The inkless fingerprint developing coating can be of any type known in the art, such as that described in U.S. Pat. Nos. 4,029,012 and 4,182,261 to Smith, III et al., U.S. Pat. Nos. 4,379,178 and 4,699,077 to Meadows et al., U.S. Pat. No. 5,462,597 to Jubrian and U.S. Pat. No. 5,454,600 to Floyd, all of which are incorporated herein by reference. A preferred "inkless" fingerprint kit is available from Identicator Corporation, which includes a pad-type applicator 20 as shown, for example, in FIG. 2, that contains a clear non-toxic organic gel inkless fingerprint material.

When the applicant has completed entering the information on the form 10, the applicant will place his or her finger onto the applicator 20. In doing so, some of the gel material will adhere to the person's finger upon contact. The applicant can then place his or her finger onto the fingerprint receiving area 16 on the application form 10. The coating adhering to the finger will react with the fingerprint developing coating present in the fingerprint receiving area 16 to form an image of the fingerprint of the applicant's finger. It is noted that the fingerprint image is formed by the combining of the material in the applicator 20 with the material described above as the "developing coating" 18. Hence, the materials present on the fingerprint receiving area 16 can instead be in the applicator 20 and vice-versa.

Figure 3:
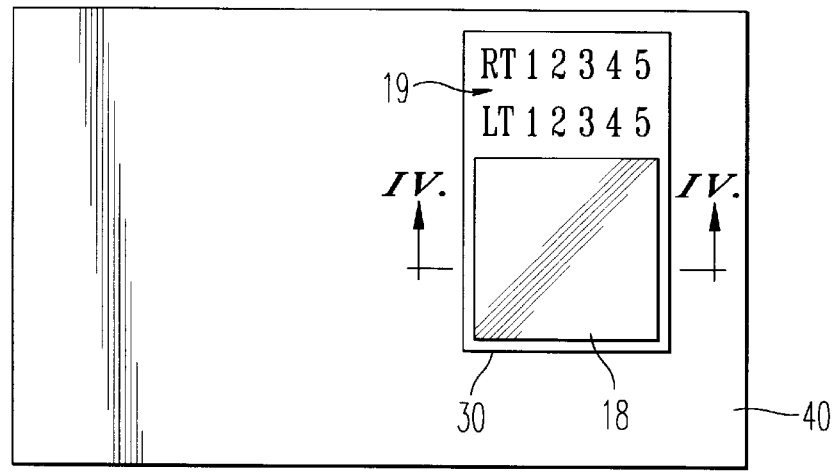
FIG. 3 is a top plan view of an example of another form used in accordance with the present invention.
Figure 4:
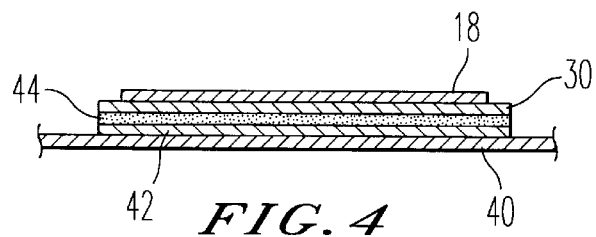
FIG. 4 is a partial cross sectional view of the fingerprint image receiving area of the form shown in FIG. 3.
Figure 5:
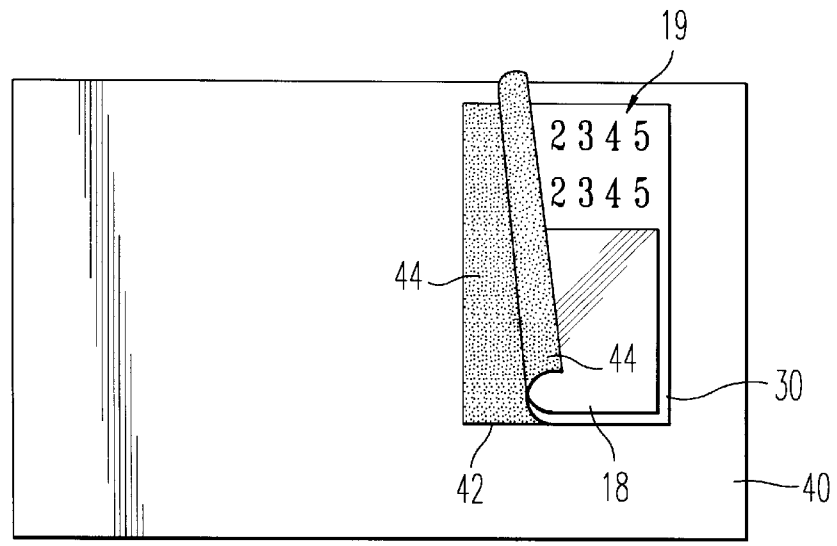
FIG. 5 is a top plan view of the form shown in FIG. 3 with the fingerprint receiving area being partially removed from the form.

Alternatively, the fingerprint developing coating 18 may be applied to another substrate 30 of another medium 40 as shown, for example, in FIGS. 3–5. That is, as shown in FIGS. 3 and 4, in particular, a medium 40, which may be made of any suitable material such as paper, thermal coated paper, or the like, can be provided with a release layer 42 and a permanent pressure sensitive adhesive layer 44 of the type used, for example, in peel-away labels known in the art. The substrate 30 having the fingerprint developing coating 18 thereon is removably attached to the release layer 42 by the permanent pressure sensitive adhesive layer 44 as illustrated. Of course, as discussed above, the material on the substrate 30 can instead be in the applicator and vice-versa, if desired.

Accordingly, as shown in FIG. 5, after the applicant has applied a finger to the applicator 20 and subsequently to the fingerprint developing coating 18 on the substrate 30 to form the fingerprint image, the substrate 30 having the fingerprint image can be peeled away from the release layer and applied to the fingerprint receiving area 16 on the form 10 (FIG. 1). The portion of the pressure sensitive adhesive layer 44 remaining on the surface of the substrate 30 opposite to the surface having the fingerprint developing coating 18 will adhere to the surface of the form having the fingerprint receiving area 16. Hence, the substrate 30 having the fingerprint image will become attached to the fingerprint receiving area 16 of form 10. Of course, the form 10 can include multiple fingerprint receiving areas which include the fingerprint developing coating 18 directly thereon, receive a substrate 30 having the fingerprint developing coating thereon, or both.

It is noted that in accordance with the present invention, designator information 19 identifying the finger that was used to make the fingerprint image will be provided on the substrate 30 if the fingerprint developing coating 18 is present on the substrate 30, or at an area near the fingerprint receiving area 16 on the form 10 if, for example, the fingerprint developing coating 18 is present directly on the fingerprint receiving area 16 of the form 10. This designator information can be, for example, the letters "RT" followed by numerals 1 through 5, which represent the right hand and fingers 1 through 5 with "1" being the thumb, and the letters "LT" followed by numerals 1 through 5 which represent the left hand and fingers 1 through 5 on that hand in a similar manner. The person providing the fingerprint sample, or the insurance agent, for example, can circle the appropriate number and hand designator ("RT" or "LT") to positively identify the finger and hand from which the fingerprint sample was obtained.

It is further noted that in accordance with the present invention, a coloring agent or material can be added to the inkless fingerprint coating in the applicator pad 20, the fingerprint developing coating 18, or both, so that a colored fingerprint image will appear when the finger having coating from applicator 20 is applied to the substrate having the fingerprint developing coating 18. Also, in accordance with the present invention, materials or chemicals can be added to the inkless fingerprint coating in the applicator pad 20, the inkless fingerprint developing coating 18, or both, so that the fingerprint image formed will be visible or substantially invisible to the human eye under normal lighting conditions, but will fluoresce when irradiated by ultraviolet light, for example.

After the fingerprint image has been provided in the fingerprint image receiving area 16 in the manner described above, the insurance agent can file the insurance form application 10 in accordance with the insurance company's normal procedures. Of course, if the application form 10 is for other purposes, such as an employment application, checking account application, and so on, the application form 10 can be handled as appropriate. The completed application form 10 having the fingerprint image could, of course, be photocopied.

The fingerprint sample on the application form 10 can thus be used as a reference fingerprint sample to verify the identity of the person who has completed the application form 10 at a later date. For instance, prior to issuing a life insurance policy, many insurance companies require that an applicant receive a physical examination, especially if the applicant is attempting to obtain a very large life insurance policy. However, as discussed above, conventional methods have been ineffective in positively verifying whether the person undergoing the physical examination is indeed the person who completed the application form 10.

Figure 6:
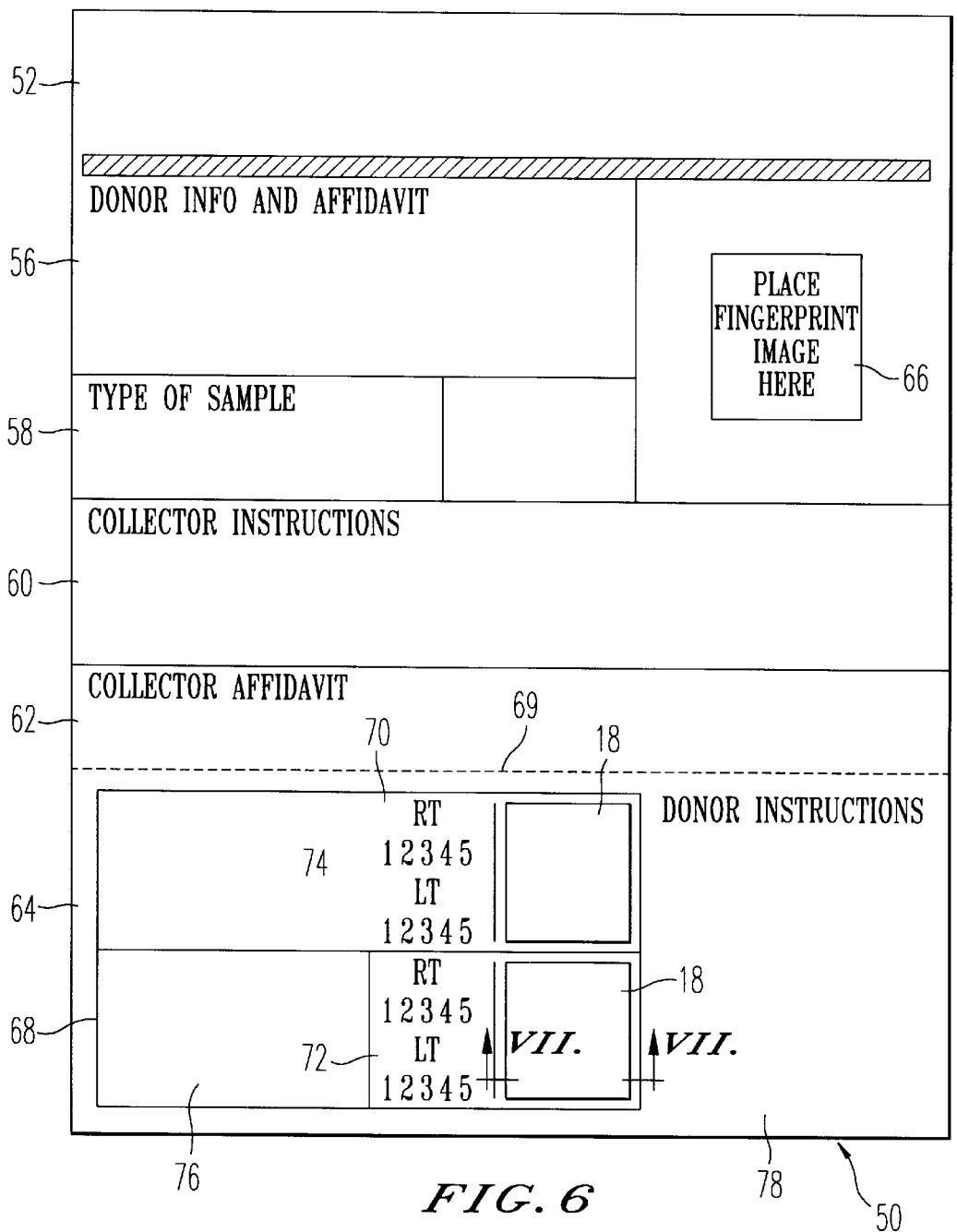
FIG. 6 is a top plan view of an example of another form having at least one fingerprint receiving area which is used in a system according to an embodiment of the present invention.

According to an embodiment of the present invention, the facility responsible for performing the physical examination can use a form 50, as shown in FIG. 6, when collecting specimens, such as blood, urine, and the like, from the applicant. Preferably, the form 50 is a chain of custody document provided by Wallace, Inc.

The form 50 includes a front side 52, as shown in FIG. 6, including the various sections described below, and a back side 54 (not shown), which includes, for example, information about the form 50 and its various uses. Specifically, the front side 52 includes an information section 56, a specimen type section 58, an instructional information section 60, a signature section 62, a donor section 64, and a fingerprint receiving area 66.

The information section 56 is an area in which personal information about the applicant, such as the applicant's name, address, date of birth, and so on, can be entered. In the specimen type section 58, the type of specimen being obtained can be indicated, along with, for example, the reasons for obtaining the specimen (e.g., life insurance, pre-employment physical examination, and so on). The instructional information section 60 includes written text for instructing the person taking the specimen how to complete the form properly. The signature section 62 is the location at which the person collecting the specimen can enter his or her name, along with the date and time that the specimen was collected.

The donor section 64 has areas in which at least one fingerprint sample can be obtained in a manner similar to that described above, and the fingerprint receiving area 66 is the area at which the fingerprint sample will be retained on the form 50. Specifically, the donor section 64 has a fingerprint sample area 68 at which at least one fingerprint of the person giving the sample will be obtained. In this example, the donor section 64 is separated from the remainder of the form 50 by a series of perforations 69 which enable the donor section 64 to be easily disconnected from the remainder of the form 50.

The fingerprint sample area 68 in this example includes two fingerprint sampling substrates 70 and 72 on which an inkless fingerprint developing coating 18, such as that described above with regard to the form in FIG. 1, is provided. Of course, any practical number of substrates can be present in the fingerprint sample area 68.

Figure 7:
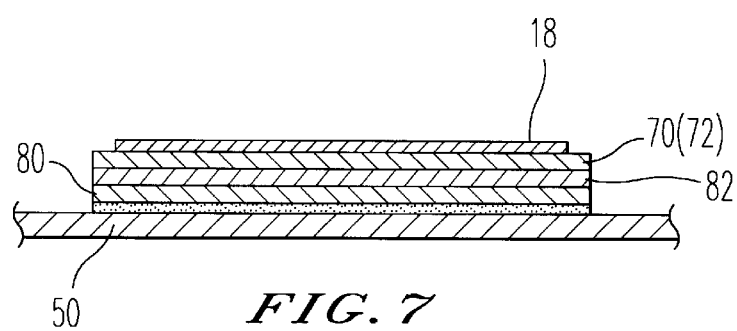
FIG. 7 is a partial cross sectional view of the fingerprint image receiving area of the form shown in FIG. 6.

As shown in FIG. 7, in this example, the form 50, which may be made of any suitable material such as paper, thermal coated paper, or the like, can be provided with a release layer 80 and a permanent pressure sensitive adhesive layer 82 of the type used, for example, in peel-away labels known in the art. The substrates 70 and 72 having the fingerprint developing coating 18 thereon are removably attached to the release layer 80 by the permanent pressure sensitive adhesive layer 82 as illustrated.

Figure 2:
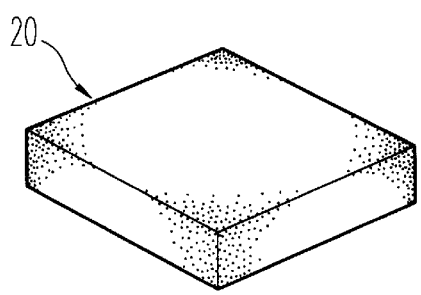
FIG. 2 is a perspective view of an applicator pad for applying a coating onto a person's finger which is used to form a fingerprint image at the fingerprint receiving area on the form shown on FIG. 1.

Accordingly, after the applicant has provided the necessary samples (e.g., blood and urine), the applicant will be requested to apply a finger to an applicator 20 as described with respect to FIG. 2 above, and subsequently to the fingerprint developing coating 18 on the substrates 70 and 72 to form the fingerprint images. It is noted that the fingerprint used to make the fingerprint images on substrates 70 and 72 should be the same finger that was used to made the fingerprint image on form 10 as discussed above. Hence, in this example, the substrates 70 and 72 each include a finger identifier 74 similar to finger identifier 19 described above with regard to form 10. The person providing the fingerprint sample, or the person collecting the sample, can circle the appropriate letters and numbers corresponding to the hand and finger from which the fingerprint samples are being taken. It is also noted that in this example, an information section providing written information pertaining to the purpose of the form is provided on a substrate adjacent to substrate 72, and another information section 78 is present in donor section 50 which provides written instructions indicating how the form 50 is to be completed.

Figure 8:
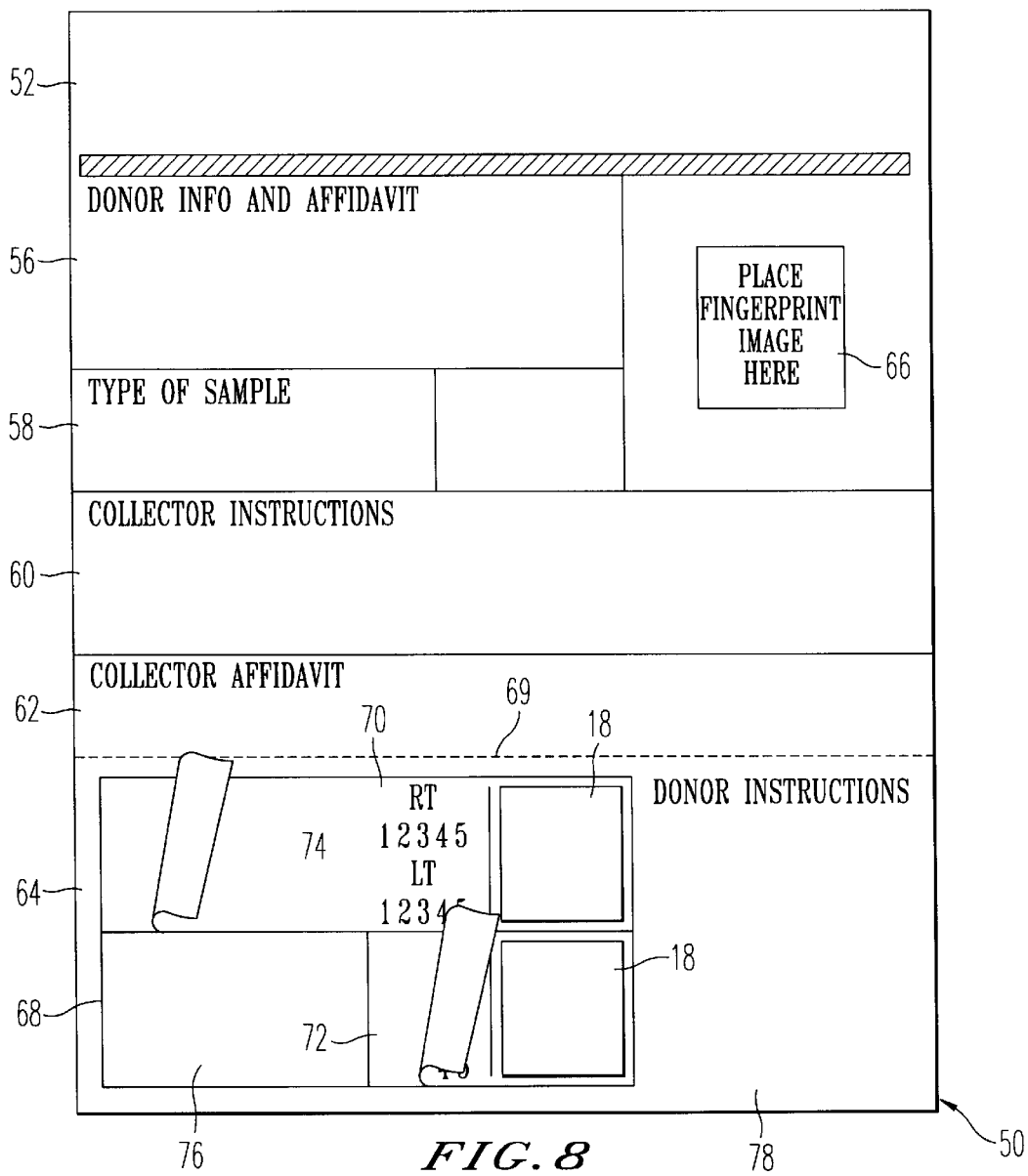
FIG. 8 is a top plan view of the form shown in FIG. 6 with the fingerprint receiving areas being partially removed from the form.

As shown in FIG. 8, the substrates 70 and 72 having the fingerprint image can then be peeled away from the release layer 80 and used in the following manner. One of the substrates 70, for example, can be applied to the specimen jar (not shown) in which a specimen has been provided by the applicant. The portion of the permanent pressure sensitive adhesive layer 82 remaining on the substrate 70 will cause the substrate to attach to the jar. The other substrate 72 can be applied to the fingerprint receiving area 66 of the form 50. The portion of the permanent pressure sensitive adhesive layer 82 remaining on the substrate 72 will cause the substrate to attach to the fingerprint receiving section 66 of the form 50. Also, another substrate like substrates 70 and 72 can be used to receive a fingerprint image in the manner described above, and that further substrate can be forwarded to the institution keeping the form 10 on file, or the form 10, or copy of the form 10, can be sent to the institution storing forms 50. That further substrate can, for example, be attached to the form 10 so that the fingerprint sample on that substrate can be immediately compared with the fingerprint image already on the form 10 in the manner discussed below.

Alternatively, the fingerprint receiving section 66 may have the fingerprint developing coating 18 directly applied thereon. In this event, the fingerprint sample to remain on the form 50 is taken directly at the fingerprint receiving area 66 in a manner similar to that in which the fingerprint samples are taken as described above. Also, the substrates 70 and 72 need not be attached to the form 50 as shown, but can be attached to another substrate in a manner similar to substrate 30 discussed above with regard to FIGS. 3–5. Of course, the form 50 can have multiple fingerprint receiving sections 66 having the developing coating 18 thereon, or which receive substrates having the fingerprint developing coating 18 thereon like substrates 70 and 72, or could have the fingerprint coating 18 thereon and be capable of receiving another substrate having the fingerprint developing coating 18 thereon.

It is further noted that in accordance with the present invention, a coloring agent or material can be added to the inkless fingerprint coating in the applicator pad 20, the fingerprint developing coating 18, or both, so that a colored fingerprint image will appear when the finger having coating from applicator 20 is applied to the substrate having the fingerprint developing coating 18. Also in accordance with the present invention, materials or chemicals can be added to the inkless fingerprint coating in the applicator pad 20, the inkless fingerprint developing coating 18, or both, so that the fingerprint image formed will be invisible or substantially invisible to the human eye under normal lighting conditions, but will fluoresce when irradiated by ultraviolet light, for example.

Once the fingerprint image has been captured on the form 50 as described above, form 50 can be stored by the specimen collecting agency, or the institution for which the application form 10 has been completed (e.g., the insurance company, potential employer, and so on), in the normal manner or in any desired manner. Hence, if the identity of the individual who completed the application form 10 needs to be verified (e.g., prior to taking action on the application or if suspicion ever arises concerning the identity of the individual who completed the application form 10 versus the identity of the individual providing the specimen samples), the fingerprint images on forms 10 and 50 can be compared to each other to determine if they match.

Figure 9:
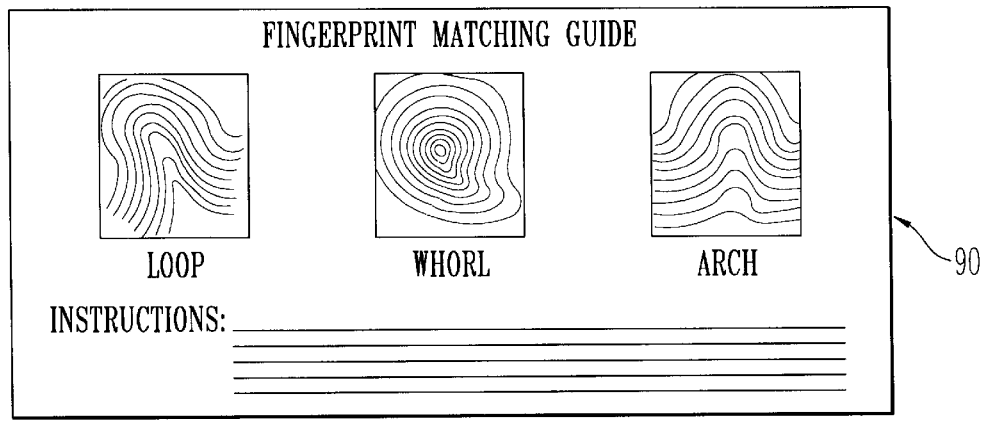
FIG. 9 is a top plan view of a fingerprint comparison form used in conjunction with the system and method according to the present invention.

In order to aid in the comparison of the fingerprints, a form 90 as shown in FIG. 9 can be used. This form 90 was developed by Wallace, Inc. and includes information illustrating the three basic types of fingerprints patterns (i.e., loop, whorl, and arch), and can be used in accordance with the system and method of the present invention to facilitate manual comparison between the fingerprint image on form 10 and fingerprint image on form 50. That is, the application form 10 including one of the fingerprint images can be brought together with the form 50 having the other fingerprint image or images, and the images on both forms can be visually compared by an individual or, if desired, a specialist such as latent print examiner from a law enforcement agency. Specifically, the critical points of the fingerprint images can be compared with each other to determine whether the images match. The form 90 can be used to assist in comparing these critical points. Of course, the fingerprint images on the forms 10 and 50 can be photocopied, enlarged, and so on to aid in the comparison.

Figure 10:
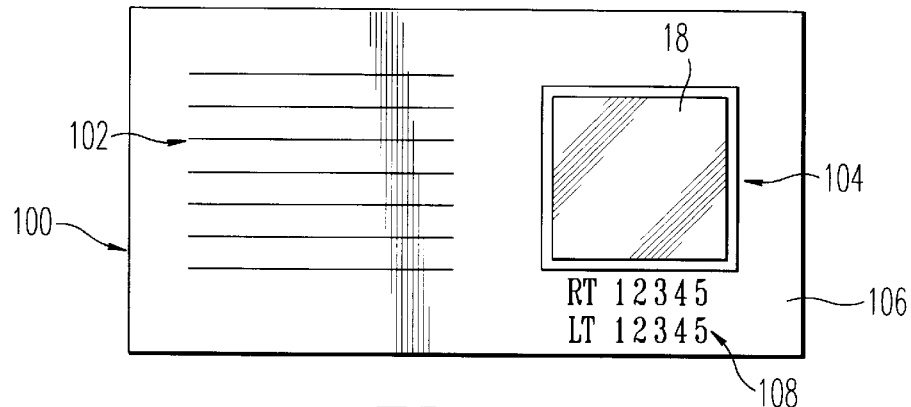
FIG. 10 is a top plan view of a fingerprint matching card used in conjunction with the system and method according to the present invention.

Additionally, in order to aid in the comparison of the fingerprints, a form 100 as shown in FIG. 10 can be used. This form 100 was developed by Wallace, Inc. and includes an information section 102 in which information pertaining to the person providing the specimen (e.g., name, address and so on) is entered, and a window portion 104 on which a fingerprint image of that person is captured. Specifically, the window portion 104 includes an opening in the form 100 through which light can pass. The form 100 and in particular, the window portion 104, is coated with a laminate 106 that is transparent or substantially transparent to visible light. This laminate can be any type of laminate known in the art.

The portion of the laminate at the window portion 104 has an inkless fingerprint developing coating 18 thereon. Therefore, when the person is providing the specimen, such as blood, urine, and the like, in the manner as described above with regard to form 50 shown in FIG. 6, the person will also place his or her finger on the applicator 20 (FIG. 2) and onto the coating 18 so that a fingerprint image will form in the window portion 104 of form 100. Form 100 further includes a designator 108, similar to designators 19 and 74, which is used to identify the finger providing the fingerprint sample in window portion 104. The finger used to provide the sample in window section 104 must be the same finger that is used to provide the samples on substrate 70 and 72 on form 50, as well as on substrate 16 on form 10 (FIG. 1).

It is noted that the fingerprint images formed on the window portion 104 by the combining of the material in the applicator 20 with the material described above as the "developing coating" 18. Hence, the materials present on the window portion 104 can instead be in the applicator 20 and vice versa.

Figure 11:
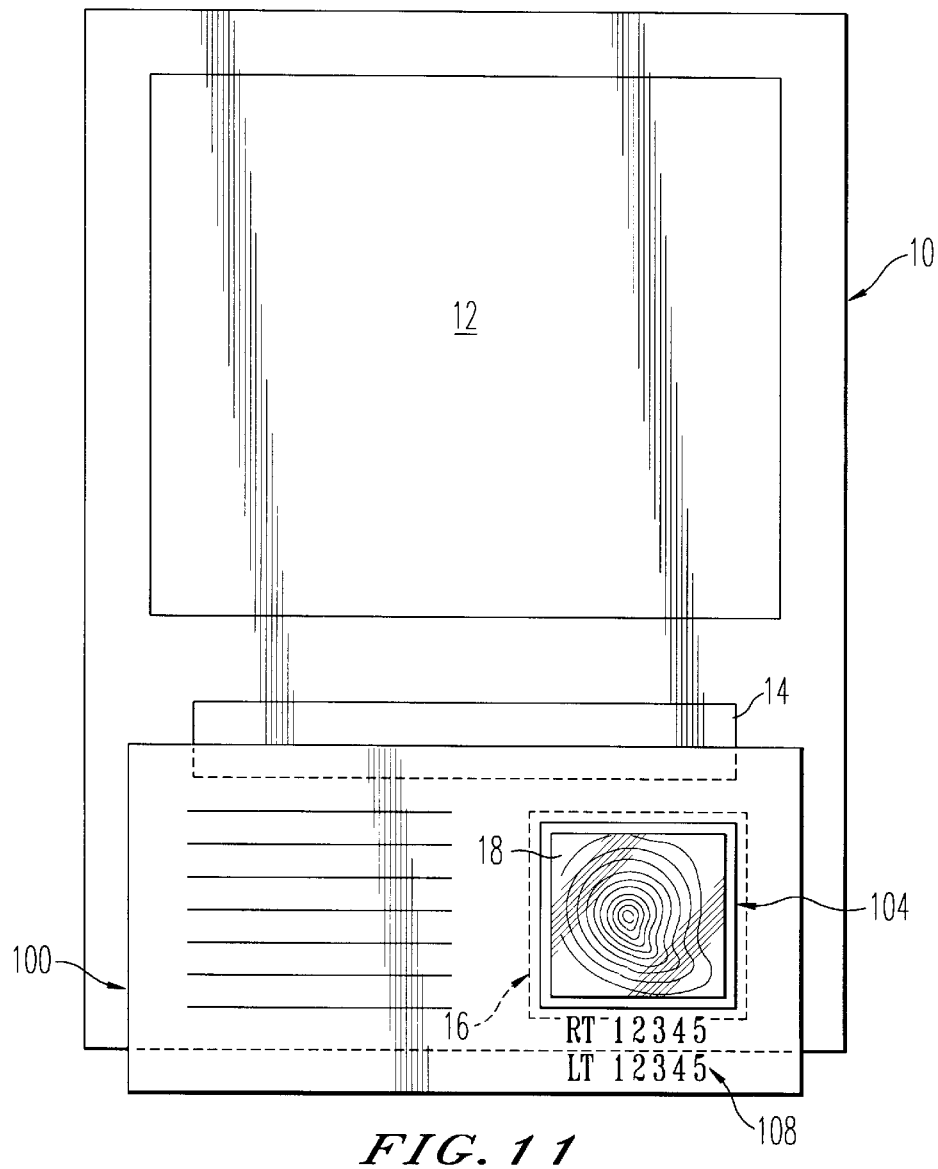
FIG. 11 illustrates the use of the fingerprint matching card shown in FIG. 10 in is accordance with the present invention.

The form 100 can then be forwarded to the organization, such as the insurance agency, that is the custodian of form 10. As shown in FIG. 11, the fingerprint image in fingerprint receiving area 16 on form 10 can be immediately compared with the fingerprint image in window portion 104 on form 100 by overlaying form 100 on form 10 such that the fingerprint images align or substantially align with each other. The person aligning the fingerprint images can therefore immediately determine whether the fingerprint images match and thus, can ascertain whether the same person provided both fingerprint images. Naturally, form 100 can be overlaid on any form to compare the fingerprint image on window section 104 to another fingerprint image on the other form.

Additionally, in order to aid in the comparison, the fingerprint images that are made on fingerprint receiving area 16 on form 10 and window portion 104 on form 100 can be of a different color. That is, different coloring agents can be added to the fingerprint developing coating 18 on forms 10 and 100 so that, for example, the fingerprint image appearing on form 10 will be blue while the fingerprint image appearing in the window portion 104 on form 100 will be yellow. When the yellow image on form 100 is laid over the blue image on form 10, a green fingerprint image will appear visible to the person performing the overlaying of the forms. If that green fingerprint image appears, the person performing the overlaying will be able to ascertain that both fingerprint images match. However, if the green image is distorted or areas of yellow and blue remain, the person performing the overlaying will be able to ascertain that the two fingerprint images do not match.

Figure 16:
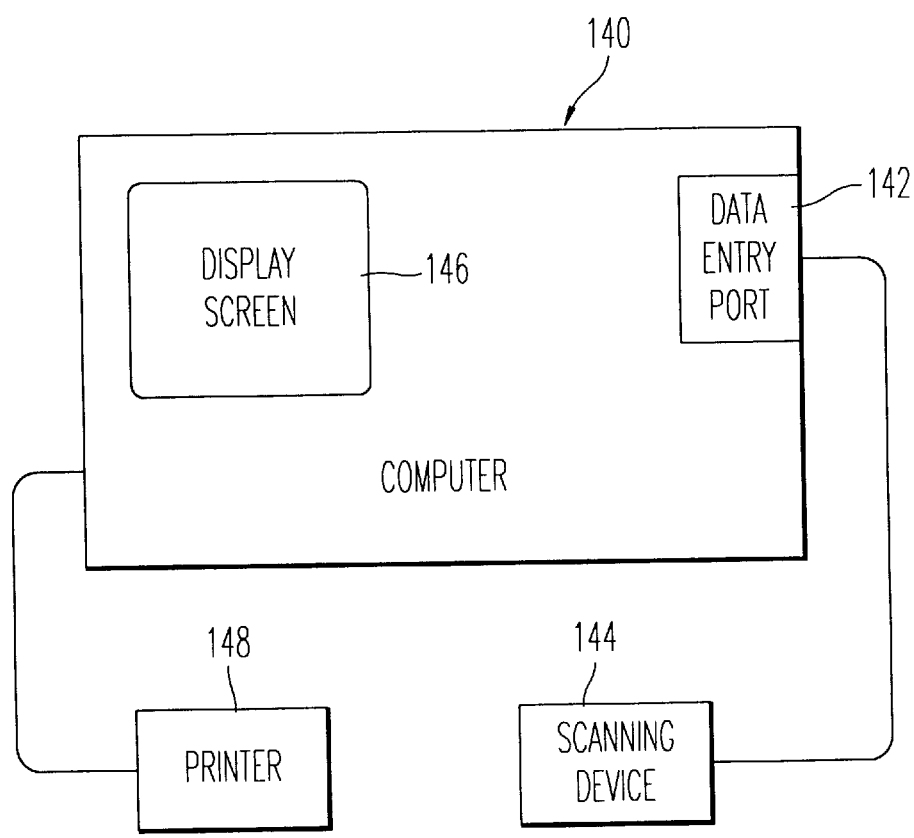
FIG. 16 is a schematic illustration of a computer for use in comparing the fingerprint images on the forms illustrated, for example in FIGS. 1 and 6.

Alternatively, the fingerprint images on forms 10 and 50 can be compared through the use of a computer 140, as shown in FIG. 16. Specifically, a computer program, such as IDSK (16 bit) or IDSK (32 bit) provided by Identicator Corporation, can be modified for use with any conventional computer 140 having a data entry port 142. That is, the images of the fingerprints on forms 10 and 50 can be scanned by a conventional document scanning device 144 which converts the images into data readable by a computer 140. The images can be scanned by the same scanning device 144 or, for example, by different scanning devices (e.g., the image on the form 10 can be scanned by the organization storing the form 10, and then the data representing the scanned image can be forwarded to the institution storing the form 50, or vice-versa). The data representing the fingerprint images can thus be entered into the computer 140, for example, by a connection between the data entry port 142 of the computer 140 and the scanning device 144.

The computer program will be run by the computer 140 and thus control the computer to compare the critical points of the fingerprint images and/or minutiae to determine whether those critical points match. The computer 140 can then provide an indication, for example, on a display screen 146, a printer 148 or the like, indicating whether the fingerprint images on forms 10 and 50 match. Accordingly, if the fingerprints match, it can be presumed that the individual providing the specimen is the same individual who is indicated as the applicant on form 10 and who provided the fingerprint sample on both forms 10 and 50. However, if the fingerprints do not match, this suggests that the person providing the specimen is different from the person who provided the fingerprint sample on form 10. Accordingly, the entity for which the application form 10 was completed (e.g., insurance company, employer, and so on) can use this evidence of non-matching between the fingerprints to establish a case of fraud against the applicant who completed the application form 10.

As discussed above, the application form 10 can be any type of application form, such as an employment application, checking or banking account application, vehicle rental application and the like. For example, many companies require that a perspective employee submit to a physical examination and, in particular, a drug screening test.

Hence, the company can use a application form 10 to obtain a sample of the job applicant's fingerprint in the manner discussed above. The facility performing the drug screening test can then use form 50, as shown in FIG. 6, in the manner described above to obtain a fingerprint sample of the person undergoing the physical examination who is providing samples such as urine, blood and so on. Alternatively, instead of providing a fingerprint sample on the employment application when initially completing the employment application, the job applicant can be asked to provide a fingerprint sample on a form 10, form 30 or the like, if suspicion arises as to the identity of the person undergoing the physical exam. The fingerprint samples on forms 10 and 50 can be compared to each other manually or through the use of a computer, as discussed above, to verify that the person completing application form 10 is the same person who underwent the physical examination. If those fingerprint samples do not match, it can be concluded that the job applicant used a stand-in to undergo the physical, and hence, action can then be taken against the applicant.

The form 100 can also be used to compare the fingerprint images during the interviewing process. For example, as a final verification of the applicant's identity, during the last interview when the applicant is about to be offered employment, the applicant can be requested to provide a fingerprint sample on form 100. The fingerprint sample on form 100 can then be compared to the fingerprint samples on forms 10 and 50 by overlaying form 100 over those forms in the manner described above with regard to FIG. 11. The person performing the interview can then immediately verify for certain that the applicant is indeed the person who completed the application form 10 and completed form 50 when providing the specimens.

The present invention further can be used in the credit card and banking environment. Specifically, the application form 10 can be used in the manner described above to obtain a fingerprint sample from an applicant opening a banking or checking account at a financial institution. Then, when a person attempts to cash a check issued in the applicant's name at that institution, the person cashing the check can be requested to provide a fingerprint sample on the check. The check can include a fingerprint developing coating 18 and the fingerprint sample can be provided directly on the image in the manner described above. Alternatively, a separate substrate, such as that described with regard to FIGS. 3–5, can include the fingerprint developing coating 18, and that substrate can be attached to the check in a manner similar to that in which the substrate 30 is attached to form 10 as described above. If suspicion ever arises regarding the person cashing the check, the fingerprint sample on the check can be compared either manually or by a computer (e.g. computer 140 described above) to the fingerprint sample on the application form 10 to determine if they match. Provided the individual uses the same finger to mark each document, if the fingerprint samples do not match, it can be ascertained that the person cashing the check is not the person holding the account, and appropriate action can be taken.

Figure 12:
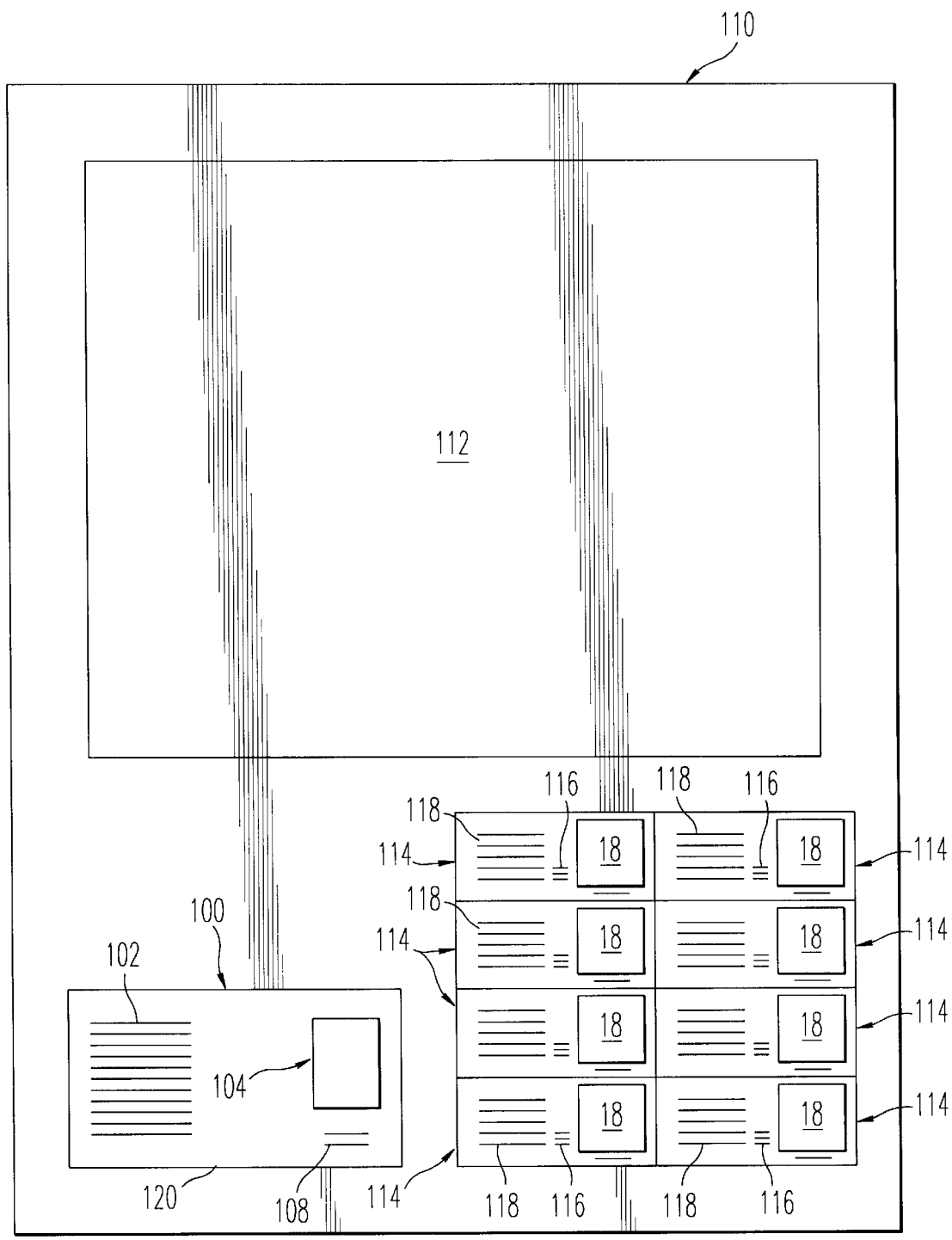
FIG. 12 is a top plan view of another form having at least one fingerprint receiving area and a removable fingerprint matching card in accordance with an embodiment of the present invention.

The present invention further can be used when a person is donating blood to be given to the person during an operation. That is, as shown in FIG. 12, a form 110 can be used when the person is donating the blood. The form 110 includes an information section 112 in which the person's name, address, date of birth, blood type, social security number, and so on, can be entered. This form further includes a plurality of substrates 114, which are removably attached to the form 110 in a manner similar to that in which substrate 30 is attached to medium 40, or in which substrates 70 and 72 are attached to form 50. Those substrates 114 each include fingerprint developing material 18 and designators 116 which are similar to designators 19, 74 and 108 which can be used to identify the finger from which the fingerprint image has been taken. Each of the substrates 114 further include information sections 118 in which information pertaining to the blood donor, such as name, address, date of birth, blood type, and so on, can be entered.

Figure 13:
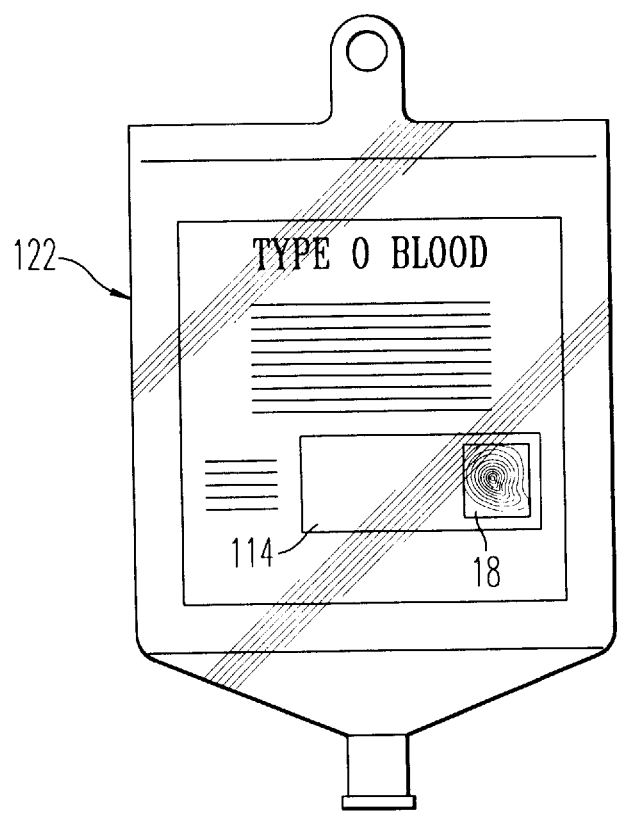
FIG. 13 is a top plan view showing a fingerprint receiving area of the form shown in FIG. 12 as applied to a sample or specimen container in accordance with the present invention.

Form 110 further includes form 100 which can be attached to form 110 in a manner similar to that in which substrate 30 is attached to form 10. Alternatively, form 100 can be attached to form 110 by perforations 120 which surround form 100 and enable the form 100 to be punched out of the form 110. When the person donates blood for the first time, the person will complete the information in information sections 112 and 102, and provide a fingerprint sample on window portion 104 of card 100. The person will also provide a fingerprint sample on one of the substrates 114, and complete the information section 118 and designator 116 on that substrate. When the person donates the blood, the substrate 114 having the fingerprint image thereon will be removed from form 100 and attached to the blood bag 122 as shown in FIG. 13 by an adhesive on the back of the substrate, or in any suitable manner. The blood bag will then be stored in the appropriate manner. Each time the person donates blood, the person will provide a new fingerprint image on one of the substrates 30, and that substrate will be attached to the bag in which the blood is stored. At the end of all the donations, the form 100 will be removed from form 110 and given to the person.

When the person enters the hospital for his or her operation, the person will present form 100 to the admitting nurse, for example. The blood donated by that person will then be pulled from storage and prepared for transfusion during that person's operation. As a final verification, the form 100 can be laid over each of the blood bags 120 so that the fingerprint inage on window portion 104 is aligned or substantially aligned with the fingerprint image on substrate 114 attached to the blood bag. If the images are determined to match, then it can be ascertained for certain that the person who presented form 100 is the person who donated the blood stored in blood bags 120. Accordingly, the chance that the wrong blood will be given to the person is substantially minimized.

Additionally, in all of the above embodiments, the applicator 20 can be attached to the form that is being used to collect a fingerprint sample. For example, the applicator can be an applicator packet 130 having a base 132, on which an inkless fingerprint material is disposed, and a clear removable film 134 covering the material, as shown in FIG. 14. When the fingerprint image is to be formed, the clear film 134 can be peeled away from the base 132 to expose the material as shown in FIG. 15. The person completing the form can then place a finger on the material as he or she would with the usual applicator 20 as shown in FIG. 2. The person then places that finger on the fingerprint receiving area, such as area 16 on form 1. As with all of the embodiments discussed above, the material described as the "developing coating" can instead be in the applicator, and vice-versa.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A kit for collecting fingerprint information of a person completing an application, comprising:

at least a portion of the application, configured as a first document, comprising a first substrate having a first identification area for receiving information pertaining to the person, and a fingerprint information receiving area for receiving thereon a fingerprint image of a finger of the person; and a second document comprising a second substrate having a second identification area, different in configuration from the first identification area, for receiving information pertaining to the person which includes information different from that received in the first identification area, and a fingerprint information receiving area for receiving thereon a fingerprint image of the finger of the person;

the first and second documents being configured for comparison of the fingerprint image in the fingerprint information receiving area of the first document with the fingerprint image in the fingerprint information receiving area of the second document to determine whether the fingerprint images match.

2. A kit as claimed in claim 1, wherein the fingerprint information receiving areas of the first and second substrate each bear an inkless fingerprint coating for developing an image of a fingerprint of the finger of the person upon contact of the coating by the finger.

3. A kit as claimed in claim 1, further comprising a fingerprint collection medium having a third substrate bearing an inkless fingerprint coating for developing an image of a fingerprint of the finger of the person upon contact of the coating by the finger, the fingerprint collection medium being configured for attachment to the fingerprint information receiving area of the first substrate; and wherein the fingerprint information receiving area of the second substrate bears an inkless fingerprint coating for developing an image of a fingerprint of the finger of the person upon contact of the coating by the finger.

4. A kit as claimed in claim 1, further comprising a fingerprint collection medium having a third substrate bearing an inkless fingerprint coating for developing an image of a fingerprint of the finger of the person upon contact of the coating by the finger, the fingerprint collection medium being configured for attachment to the fingerprint information receiving area of the second substrate; and wherein the fingerprint information receiving area of the first substrate bears an inkless fingerprint coating for developing an image of a fingerprint of the finger of the person upon contact of the coating by the finger.

5. A kit as claimed in claim 1, further comprising first and second fingerprint collection mediums, each having a substrate bearing an inkless fingerprint coating for developing an image of a fingerprint of the finger of the person upon contact of the coating by the finger, the substrates of first and second fingerprint collection mediums being configured for attachment to the fingerprint information receiving areas of the first and second substrates, respectively.

6. A kit as claimed in claim 1, further comprising a fingerprint collection medium having a third substrate bearing an inkless fingerprint coating for developing an image of a fingerprint of the finger of the person upon contact of the coating by the finger, the third substrate being removably secured to the fingerprint collection medium, such that the third substrate is configured for removal from the fingerprint collection medium and for attachment to the fingerprint information receiving area of one of the first and second substrates.

7. A kit as claimed in claim 6, wherein the fingerprint collection medium is a portion of the second document, and the third substrate is configured for attachment to the fingerprint information receiving area of the second substrate.

8. A kit as claimed in claim 1, wherein said at least a portion of the application comprises at least a portion of an insurance application form.

9. A kit as claimed in claim 1, wherein the fingerprint image received on the fingerprint information receiving area of at least one of the first and second substrates fluoresces when irradiated with ultraviolet light.

10. A kit as claimed in claim 1, further comprising a device for use in comparing the fingerprint images on the fingerprint information receiving areas of the first and second substrates to determine whether the fingerprint images match each other.

11. A kit as claimed in claim 10, wherein the device is a computer system comprising a data entry apparatus to enter into the computer system first and second data representing the fingerprint images on the fingerprint information receiving areas of the first and second substrates, respectively, the computer comparing the first and second data with each other to determine whether the fingerprint images match each other.

12. A kit as claimed in claim 1, further comprising third document comprising a third substrate having a fingerprint information receiving area for receiving thereon a fingerprint image of the finger of the person, the fingerprint information receiving area being substantially transparent to visible light, the third document being configured for placement proximate to the first document such that the fingerprint image on the fingerprint information receiving area of the third substrate is substantially aligned with the fingerprint image in the fingerprint information receiving area on the first document.

13. A kit as claimed in claim 12, wherein the third document has an opening therein, and the fingerprint information receiving area of the third document is aligned with the opening such that visible light can pass through the opening and the fingerprint image formed on the fingerprint information receiving area of the third document.

14. A kit as claimed in claim 12, wherein the fingerprint information receiving area of the first document comprises a material to create the fingerprint image thereon of a first color, and the fingerprint information receiving area of the third document comprises a material to create the fingerprint image thereon of a second color, different from the first color.

15. A kit as claimed in claim 1, wherein said at least a portion of the application comprises at least a portion of an employment application form.

16. A kit as claimed in claim 1, wherein said at least a portion of the application comprises at least a portion of a checking account application form.

17. A kit as claimed in claim 1, wherein said at least a portion of the application comprises at least a portion of a vehicle rental application form.

18. A kit for comparing fingerprint information of a person, comprising:

a first document comprising a first substrate having a first fingerprint information area for receiving thereon a fingerprint image of the finger of the person; and a second document comprising a second substrate having a second fingerprint information receiving area for receiving thereon a fingerprint image of the finger of the person, the second fingerprint information receiving area of the second substrate being substantially transparent to visible light;

the first and second documents being configured for placement proximate to each other such that their respective fingerprint images are substantially aligned with each other to verify that the fingerprint image on the second fingerprint information receiving area of the second substrate corresponds to the fingerprint image on the first fingerprint information receiving area of the first substrate.

19. A kit as claimed in claim 18, wherein the second document has an opening therein and the second fingerprint information receiving area of the second substrate is aligned with the opening.

20. A kit for comparing fingerprint information of a person, comprising:

a first document comprising a first substrate having a first fingerprint information area for receiving thereon a fingerprint image of the finger of the person; and a second document comprising a second substrate having a second fingerprint information receiving area for receiving thereon a fingerprint image of the finger of the person, the fingerprint information receiving area of the second substrate being substantially transparent to visible light;

the first and second documents being configured for placement proximate to each other such that their respective fingerprint images are substantially aligned with each other; and wherein the fingerprint information receiving area of the first document comprises a material to create the fingerprint image thereon of a first color, and the fingerprint information receiving area of the second document comprises a material to create the fingerprint image thereon of a second color, different from the first color.

21. A kit for collecting fingerprint information of a person completing an application, comprising:

at least a portion of the application, configured as a first document, comprising a first substrate having a first identification area for receiving information pertaining to the person, and a fingerprint information receiving area for receiving thereon a fingerprint image of a finger of the person; and a second document comprising a second substrate having a second identification area for receiving information pertaining to the person, and a fingerprint information receiving area for receiving thereon a fingerprint image of the finger of the person; and a third document comprising a third substrate having a fingerprint information receiving area for receiving thereon a fingerprint image of the finger of the person, the fingerprint information receiving area being substantially transparent to visible light;

wherein the fingerprint information receiving area of the first document comprises a material to create the fingerprint image thereon of a first color, and the fingerprint information receiving area of the third document comprises a material to create the fingerprint image thereon of a second color, different from the first color;

the first and second documents being configured for comparison of the fingerprint image in the fingerprint information receiving area of the first document with the fingerprint image in the fingerprint information receiving area of the second document to determine whether the fingerprint images match; and the third document being configured for placement proximate to the first document such that the fingerprint image on the fingerprint information receiving area of the third substrate is substantially aligned with the fingerprint image in the fingerprint information receiving area on the first document.

\* \* \* \* \*